United States Patent [19]

Suzuki et al.

[11] Patent Number: 4,942,268
[45] Date of Patent: * Jul. 17, 1990

[54] PROCESS FOR PRODUCING A HALOBENZENE

[75] Inventors: Toshihiro Suzuki; Chizu Komatsu, both of Shizuoka, Japan

[73] Assignee: Ihara Chemical Industry Co., Ltd., Tokyo, Japan

[*] Notice: The portion of the term of this patent subsequent to May 23, 2006 has been disclaimed.

[21] Appl. No.: 323,845

[22] Filed: Mar. 15, 1989

Related U.S. Application Data

[63] Continuation of Ser. No. 57,650, Jun. 9, 1987, Pat. No. 4,831,199.

[30] Foreign Application Priority Data

Mar. 7, 1984 [JP] Japan ................... 59-41929
Mar. 19, 1984 [JP] Japan ................... 59-52953
May 25, 1984 [JP] Japan ................... 59-106103

[51] Int. Cl.$^5$ ............................. C07C 17/12
[52] U.S. Cl. ....................... 570/206; 570/147; 570/206; 570/207
[58] Field of Search ............. 570/206, 208, 210, 207, 570/147

[56] References Cited

U.S. PATENT DOCUMENTS 4,794,201 12/1988 Higuchi et al. ............ 570/208
4,822,933 4/1989 Suzuki et al. ............ 570/208

FOREIGN PATENT DOCUMENTS 0112722 7/1984 European Pat. Off. ............ 570/208
0118851 9/1984 European Pat. Off. ............ 570/208
0195514 9/1986 European Pat. Off. ............ 570/208
0231133 8/1987 European Pat. Off. ............ 570/208
2087536 4/1987 Japan ................................. 570/208

*Primary Examiner*—Werren B. Lone
*Attorney, Agent, or Firm*—Oblon, Spivak, McClelland, Maier & Neustadt

[57] ABSTRACT

A process for producing a halobenzene represented by the formula:

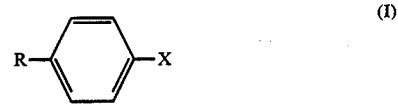

(I)

where R is a lower alkyl group, a lower alkoxy group or a halogen atom, and X is a halogen atom, which comprises halogenating a benzene represented by the formula:

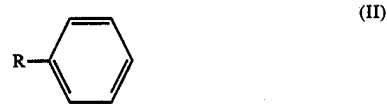

(II)

where R is as defined above, in a liquid phase in the presence of a catalyst, characterized in that the catalyst is a combination of an aliphatic carboxylic acid component and a zeolite having a SiO$_2$/Al$_2$O$_3$ molar ratio of from 3 to 8 and a pore size of from 6 to 10 Å.

13 Claims, No Drawings

PROCESS FOR PRODUCING A HALOBENZENE

This is a continuation of Ser. No. 057,650, filed June 9, 1987, now U.S. Pat. No. 4,831,199.

The present invention relates to a process for producing a halobenzene such as chlorotoluene or dichlorobenzene which is useful as a starting material for the production of medicines and agricultural chemicals. More particularly, it relates to a process for producing a p-halobenzene with high selectivity by halogenating a benzene with use of a novel catalyst.

Halobenzenes are useful as starting materials for medicines and agricultural chemicals. Particularly, there are strong demands for p-halobenzenes among them. Accordingly, there have been various studies to improve the selectivity for p-halogenation.

As a process for the liquid phase halogenation of an alkyl benzene, it has been common to conduct the halogenation in the presence of a Lewis acid catalyst such as antimony chloride, ferric chloride or aluminum chloride by means of a halogenating agent such as chlorine gas. However, such a process produces an o-chloroalkylbenzene as a major product and a m-chloro derivative and a polychloro derivative as by-products, whereby it is impossible to produce a p-chloroalkylbenzene in good selectivity as high as at least 40%. Under the circumstances, there have been various researches for the developments of catalysts to improve the selectivity for a p-chloroalkylbenzene, and there have been some proposals.

For example, there have been known a method wherein a p-chloro derivative is obtained in a selectivity of from 45 to 52% by means of a catalyst composed of a Lewis acid and sulfur or selenium, a method wherein a p-chloro derivative is obtained in a selectivity of from 55 to 60% by means of a catalyst composed of a Lewis acid and thianthrene (U.S. Pat. No. 4,031,147), and a method wherein a p-chloro derivative is obtained in a selectivity of from 52 to 60% by means of a catalyst system composed of a Lewis acid and a phenoxthine compound (U.S. Pat. No. 4,444,983). On the other hand, with respect to chlorination of chlorobenzene, there have been known a method wherein a p-dichlorobenzene is obtained in a selectivity of from 60 to 70% by reacting chlorobenzene with chlorine in the presence of an iron sulfide catalyst (GB No. 1,476,398), and a method wherein a p-dichlorobenzene is obtained in a selectivity of 72% by reacting chlorobenzene with chlorine by means of selenium or a selenium compound as a catalyst (Japanese Examined Patent Publication No. 34010/1975).

However, these conventional methods are not necessarily satisfactory as a process for the production of a p-halobenzene, because the selectivity for the p-halo derivative is low in each case.

Accordingly, it is an object of the present invention to provide a process for producing a p-halobenzene in high selectivity by a liquid phase halogenation of a benzene in the presence of a catalyst.

It has been found that the object of the present invention can be attained by using as the catalyst a combination of an aliphatic carboxylic acid component and a certain zeolite. The present invention is based on this discovery.

Namely, the present invention provides a process for producing a halobenzene represented by the formula:

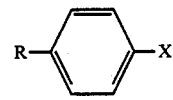
(I)

where R is a lower alkyl group, a lower alkoxy group or a halogen atom, and X is a halogen atom, which comprises halogenating a benzene represented by the formula:

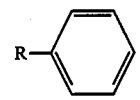
(II)

where R is as defined above, in a liquid phase in the presence of a catalyst, characterized in that the catalyst is a combination of an aliphatic carboxylic acid component and a zeolite having a $SiO_2/Al_2O_3$ molar ratio of from 3 to 8 and a pore size of from 6 to 10 Å.

Now, the present invention will be described in detail with reference to the preferred embodiments.

As the substituents R in the starting compound of the formula II used in the process of the present invention, there may be mentioned a straight chained or branched alkyl or alkoxy group, or a halogen atom such as a fluorine atom, a chlorine atom or an bromine atom. Particularly preferred is an alkyl group having from 1 to 4 carbon atoms or a chlorine atom.

In the process of the present invention, it is essential to use as the catalyst a combination of an aliphatic carboxylic acid component and a zeolite having a $SiO_2/Al_2O_3$ molar ratio of from 3 to 8 and a pore size of from 6 to 10 Å. When a zeolite with a $SiO_2/Al_2O_3$ molar ratio or a pore size being outside the above-mentioned range, is used, the selectivity for a p-halobenzene will be substantially poor.

A typical representative of the zeolite which satisfies the above conditions, is L-type zeolite, which is a crystalline aluminosilicate having a $SiO_2/Al_2O_3$ molar ratio of from 4 to 8 and a pore size of from about 7 to about 10 Å. As another example of the zeolite which satisfies the above conditions, there may be mentioned Y-type zeolite having a $SiO_2/Al_2O_3$ molar ratio of from 3 to 7 and a pore size of from about 6 to about 9 Å.

For the catalyst of the present invention, it is also possible to employ a synthetic zeolite or natural zeolite having the same X-ray diffraction spectrum as the above-mentioned L-type or Y-type zeolite. Further, the ion exchangeable cations contained in such zeolite are usually sodium or potassium, but may further include other cations. As such cations, there may be mentioned metal ions or protons belonging to Group IA, Group IIA, Group IIIA, Group IVA or Group VA of the periodic table. These cations may be of the same type or of two or more different types.

For the purpose of the present invention, the term "aliphatic carboxylic acid component" includes an aliphatic carboxylic acid and its derivatives such as a halide, anhydride or metal salt of an aliphatic carboxylic acid. As the aliphatic carboxylic acid, there may be mentioned acetic acid, propionic acid, isovaleric acid, monochloroacetic acid, monobromoacetic acid, dichloroacetic acid, trichloroacetic acid, α-chloropropionic acid, β-chloropropionic acid, difluoroacetic acid, trifluoroacetic acid, pentafluoropropionic acid or β-chlorotetrafluoropropionic acid which may be substituted or unsubstituted. The metal salt may be a sodium, potassium or barium salt of an aliphatic carboxylic acid. The halide may be a chloride or a bromide of an aliphatic carboxylic acid. Among them, aliphatic carboxylic acids and their metal salts are preferred. Among them, sodium salts or potassium salts are further preferred. Further, aliphatic carboxylic acids and their metal salts may be employed in, the form of hydrates.

The aliphatic carboxylic acid component is used in an amount of at least 1% by weight relative to the zeolite. However, from the industrial point of view, it is preferred to use the aliphatic carboxylic acid component in an amount within a range of from 3 to 30% by weight relative to the zeolite.

In the present invention, the zeolite and the aliphatic carboxylic acid component may be combined prior to the halogenation reaction. Alternatively, the zeolite and the aliphatic carboxylic acid component may simultaneously be added to the reaction system at the time of the halogenation.

The premixing may be conducted in such a manner that the zeolite is suspended in a solvent, a predetermined amount of the aliphatic carboxylic acid component is added thereto, then, the solvent is distilled off and the mixture is dried under reduced pressure.

On the other hand, in the case of combining them at the time of the reaction, the zeolite is suspended in the starting material benzene fed in the halogenation reactor, then a predetermined amount of the aliphatic carboxylic acid component is added thereto, and the mixture is stirred at a temperature lower than the boiling point, preferably from 20° to 100° C., followed by the subsequent halogenation.

The combination of the zeolite and the aliphatic carboxylic acid component can be adequately conducted by one of the above methods. However, if desired, both methods may be employed for the adequate treatment of the zeolite with the aliphatic carboxylic acid component.

To conduct the halogenation of a benzene in accordance with the process of the present invention, for instance, the zeolite treated with the aliphatic carboxylic acid component is added in an amount of at least 0.01 g, preferably from 0.1 to 10 g, per mol of the starting material benzene, and a halogenating agent is introduced into the mixture in a liquid phase while stirring the mixture at a temperature of not higher than the boiling point. In this operation, a reaction solvent may be employed as the case requires. As the halogenating agent, there may be employed any agent commonly employed for the halogenation of aromatic rings. Preferred are chlorine, bromine and sulfuryl chloride. These halogenating agents may be employed as diluted with an inert gas such as nitrogen. The reaction temperature for the halogenation is usually from 0° C. to the boiling point of the reaction mixture, preferably from 20° to 100° C. from the practical viewpoint. The reaction may be conducted under reduced or elevated pressure, but is usually conducted under atmospheric pressure.

According to the process of the present invention, it is possible to selectively and efficiently halogenate the p-position of the benzene of the formula II while suppressing the halogenation at the o-position, and to minimize the formation of by-products such as side chain-halogenated products or polyhalogenated products, whereby a highly useful p-halobenzene of the formula I can be obtained in good selectivity.

Further, according to the process of the present invention, in a case where a p-dihalobenzene is to be produced from a monohalobenzene as the starting material, it is possible to advantageously conduct the production of the monohalobenzene from benzene and the step of halogenating the monohalobenzene to the p-dihalobenzene, continuously in the same reactor.

Furthermore, according to the process of the present invention, the operation of the reaction and the subsequent after-treatment is simple, and the catalyst can be reused. Thus, the process of the present invention is suitable as an industrial process for the production of p-halobenzenes.

Now, the present invention will be described in further detail with reference to Examples. However, it should be understood that the present invention is by no means restricted by these specific Examples.

EXAMPLE 1

Into a 200 ml reaction flask equipped with a condenser, a thermometer, a stirrer and a gas supply tube, 5 g of L-type zeolite (tradename: TSZ-506, manufactured by Toyo Soda Manufacturing Co., Ltd.) and 92.1 g (1 mol) of toluene were introduced, and 1.0 g of monochloroacetic acid was added thereto. The mixture was maintained at 70° C., and stirred for 30 minutes while supplying nitrogen gas. Then, chlorine gas was supplied at a rate of 0.25 mol/hr for 4 hours to conduct the reaction while maintaining the reaction temperature at 70° C. After the completion of the reaction, the reaction product thereby obtained, was analyzed by gas chromatography, whereby it was found that the conversion of toluene was 98.3%, the production ratio of o-chlorotoluene/p-chlorotoluene (hereinafter referred to simply as "o/p ratio") was 0.262, and the selectivity of p-chlorotoluene was 74.2%.

EXAMPLE 2

The reaction was conducted in the same manner as in Example 1 except that monochloroacetic acid was added in an amount of 0.25 g, whereby the conversion of toluene was 95.3% and the o/p ratio was 0.269.

EXAMPLES 3 to 13 and COMPARATIVE EXAMPLES 1 and 2

The halogenation was conducted in the same manner as in Example 1 except that a various substituted or unsubstituted aliphatic carboxylic acid as identified in Table 1 was used instead of monochloroacetic acid, and the temperature for the treatment of the zeolite and the reaction temperature were adjusted to 50° C., 70° C. or 90° C. The results are shown in Table 1.

Further, for the purpose of comparison, the Table includes the results obtained from the cases wherein L-type zeolite as catalyst, and a combination of L-type zeolite with benzoic acid were employed.

TABLE 1

| Example | Aliphatic carboxylic acid | Zeolite treating temp. & reaction temp. (°C.) | Conversion (%) | o/p ratio |
|---|---|---|---|---|
| 3 | Acetic acid | 70 | 99.8 | 0.319 |
| 4 | α-Chloropropionic acid | 70 | 93.8 | 0.233 |
| 5 | β-Chloropropionic acid | 70 | 90.4 | 0.220 |

TABLE 1-continued

| Example | Aliphatic carboxylic acid | Zeolite treating temp. & reaction temp. (°C.) | Conversion (%) | o/p ratio |
|---|---|---|---|---|
| 6 | β-Chloropropionic acid | 90 | 92.0 | 0.325 |
| 7 | Dichloroacetic acid | 70 | 96.2 | 0.250 |
| 8 | Difluoroacetic acid | 70 | 99.4 | 0.250 |
| 9 | Trifluoroacetic acid | 70 | 99.7 | 0.344 |
| 10 | Propionic acid | 50 | 90.6 | 0.254 |
| 11 | Monobromoacetic acid | 50 | 99.4 | 0.248 |
| 12 | Monochlorodifluoroacetic acid | 50 | 99.8 | 0.248 |
| 13 | Pentafluoropropionic acid | 50 | 99.8 | 0.296 |
| Comparative 1 | None | 70 | 95.1 | 0.496 |
| Comparative 2 | Benzoic acid | 70 | 93.9 | 0.608 |

EXAMPLE 14

The halogenation was conducted in the same manner as in Example 1 except that 112.6 g (1 mol) of chlorobenzene was used as the starting material instead of toluene, dichloroacetic acid was used instead of monochloroacetic acid, and the reaction time was changed to 5 hours, whereby the conversion of chlorobenzene was 90.5%, the production ratio of o-dichlorobenzene/p-dichlorobenzene was 0.071, and the selectivity of p-dichlorobenzene was 92.7%.

EXAMPLE 15

The halogenation was conducted in the same manner as in Example 1 except that Y-type zeolite (tradename: LZ-Y82, manufactured by Union Carbide Corp., U.S.A.) was used instead of L-type zeolite, 108.1 g (1 mol) of anisole was used as the starting material instead of toluene, and difluoroacetic acid was used instead of monochloroacetic acid, whereby the conversion of anisole was 91.5%, and the production ratio of o-chloroanisole/p-chloroanisole was 0.218.

EXAMPLE 16

After the completion of the reaction in Example 1, the catalyst was recovered from the reaction mixture. By using the recovered catalyst, the halogenation was repeated 4 times in the same manner as in Example 1, whereby the reaction proceeded normally in each case and the conversion was 98.1% and the o/p ratio was 0.267.

EXAMPLE 17

Into a 200 ml reaction flask equipped with a condenser, thermometer, a stirrer and a gas supply tube, 5 g of L-type zeolite (tradename: TSZ-506, manufactured by Toyo Soda Manufacturing Co., Ltd.) and 92.1 g (1 mol) of toluene were introduced, and 1.0 g of potassium dichloroacetate was added thereto. The mixture was maintained at 50° C. and stirred for 30 minutes while supplying nitrogen gas. Then, chlorine gas was supplied at a rate of 0.25 mol/hr for 4 hours to conduct the reaction while maintaining the reaction temperature at 50° C. After the completion of the reaction, the reaction product thereby obtained, was analyzed by gas chromatography, whereby it was found that the conversion of toluene was 96.6%, the o/p ratio was 0.208, and the selectivity of p-chlorotoluene was 79.63%.

EXAMPLES 18 to 22

The halogenation was conducted at 50° C. in the same manner as in Example 17 except that a various metal salt of a substituted or unsubstituted aliphatic carboxylic acid, as identified in Table 2, was used instead of potassium dichloroacetate. The results are shown in Table 2.

TABLE 2

| No. | Metal salt of an aliphatic carboxylic acid | Conversion (%) | o/p ratio |
|---|---|---|---|
| 18 | Potassium acetate | 89.9 | 0.313 |
| 19 | Sodium dichloroacetate | 99.2 | 0.259 |
| 20 | Potassium difluoroacetate | 90.4 | 0.292 |
| 21 | Barium acetate | 91.9 | 0.322 |
| 22 | Sodium acetate (trihydrate) | 87.7 | 0.363 |

EXAMPLE 23

The halogenation was conducted in the same manner as in Example 17 except that 112.6 g (1 mol) of chlorobenzene was used as the starting material instead of toluene, and the reaction temperature was changed to 70° C., whereby the conversion of chlorobenzene was 90.5%, the production ratio of o-dichlorobenzene/p-dichlorobenzene was 0.062, and the selectivity of p-dichlorobenzene was 93.4%.

EXAMPLE 24

After the completion of the reaction in Example 23, the catalyst was recovered from the reaction mixture. By using the recovered catalyst, the operation was repeated 4 times in the same manner as in Example 23, whereby the reaction proceeded normally and the conversion was 90.1% and the production ratio of o-dichlorobenzene/p-dichlorobenzene was 0.075.

EXAMPLE 25

Into a 200 ml reaction flask equipped with a condenser, a thermometer, a stirrer and a gas supply tube, 5 g of L-type zeolite (tradename: TSZ-504, manufactured by Toyo Soda Manufacturing Co., Ltd.) and 92.1 g (1 mol) of toluene were introduced, and 0.5 g of chloroacetyl chloride was added thereto. The mixture was maintained at 50° C. and stirred for 30 minutes while supplying nitrogen gas. Then, chlorine gas was, supplied at a rate of 0.25 mol/hr for 4 hours to conduct the reaction while maintaining the reaction at 50° C. After the completion of the reaction, the reaction product thereby obtained was analyzed by gas chromatography, whereby the conversion of toluene was 98%, the o/p ratio was 0.312, and the selectivity of p-chlorotoluene was 70.38%.

EXAMPLE 26

The reaction was conducted in the same manner as in Example 25 except that chloroacetyl chloride was added in an amount of 0.25 g, whereby the conversion of toluene was 90.1% and the o/p ratio was 0.338.

EXAMPLES 27 to 32

The halogenation was conducted at 70° C. in the same manner as Example 25 except that a various benzene as identified in Table 3 was used as the starting material instead of toluene. The results are shown in Table 3.

TABLE 3

| No. | The benzene (II) | Conversion (%) | o/p ratio |
|---|---|---|---|
| 27 | Ethylbenzene | 99.6 | 0.160 |
| 28 | Cumene | 94.6 | 0.108 |
| 29 | t-Butylbenzene | 95.9 | 0.036 |
| 30 | Chlorobenzene | 94.8 | 0.076 |
| 31 | Anisole | 89.0 | 0.192 |
| 32 | Fluorobenzene | 95.3 | 0.019 |

EXAMPLES 33 to 39

The halogenation was conducted at 70° C. in the same manner as in Example 25 except that a various aliphatic carboxylic acid halide or anhydride as identified in Table 4 was used instead of chloroacetyl chloride used in Example 25. The results are shown in Table 4.

For the purpose of comparison, the table includes the results obtained by using a combination of L-type zeolite with benzoyl chloride (Comparative Example 3).

TABLE 4

| No. | Aliphatic carboxylic acid derivative | Conversion (%) | o/p ratio |
|---|---|---|---|
| 33 | Trifluoroacetic anhydride | 97.4 | 0.442 |
| 34 | Acetic anhydride | 86.3 | 0.409 |
| 35 | Acetyl chloride | 89.8 | 0.452 |
| 36 | Chloroacetyl chloride | 96.0 | 0.360 |
| 37 | Dichloroacetyl chloride | 85.2 | 0.438 |
| 38 | Bromoacetyl chloride | 82.3 | 0.442 |
| 39 | Bromoacetyl bromide | 79.7 | 0.437 |
| Comparative Example 3 | Benzoyl chloride | 86.0 | 0.696 |

EXAMPLE 40

The halogenation was conducted at 70° C. in the same manner as in Example 25 except that 35.2 g (1.0 mol) of sulfuryl chloride was dropwise added over a period of 4 hours instead of chlorine gas, and aging was conducted for 3 hours, whereby the conversion of toluene was 99.4% and the o/p ratio was 0.293.

EXAMPLE 41

After the completion of the reaction in Example 25, the catalyst was recovered from the reaction mixture. By using the recovered catalyst, the operation was repeated in the same manner as in Example 25, whereby the reaction proceeded normally, and the conversion was 98.2% and the o/p ratio was 0.320.

We claim:

1. A process for producing a halobenzene of the formula:

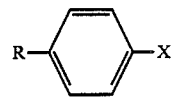

(I)

wherein R is a lower alkyl group, a lower alkoxy group, or a halogen atom selected from the group consisting of a fluorine atom, a chlorine atom and a bromine atom, and X is a halogen atom selected from the group consisting of a fluorine atom, a chlorine atom, and a bromine atom, said process comprising halogenating, with a halogenating agent which is selected from the group consisting of chlorine, bromine and sulfuryl chloride, at a temperature and pressure suitable for halogenating, a benzene compound of the formula:

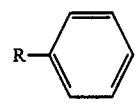

(II)

in a liquid phase in the presence of a catalyst, wherein said catalyst is a combination of a component selected from the group consisting of acidic, propionic acid, isovoleric acid, monochloroacidic acid, monobromoacidic acid, dichloroacidic acid, trichloroacidic acid, α-chloropropionic acid, β-chloropropionic acid, difluoroacidic acid, trifluoroacidic acid, pentafluoropropionic acid, β-chlorotetrafluoropropionic acid, sodium, potassium and barrium salts thereof, and a zeolite having a Si $O_2/Al_2O_3$ molar ratio of from 3 to 8 and a pore size of from 6 to Å.

2. The process of claim 1, wherein said component is potassium dichloroacetate, sodium dichloroacetate, or potassium difluoroacetate.

3. The process of claim 1, wherein said component is chloroacetylchloride.

4. The process of claim 1, wherein said zeolite is used in an amount of at least 0.01 gram per mole of said benzene compound of formula (II).

5. The process of claim 1, wherein said zeolite is used in an amount of from 0.1 to 10 grams per mole of said benzene formula (II).

6. The process of claim 1, wherein said component is used in amount of at least 1% by weight relative to said zeolite.

7. The process of claim 1, wherein said component is used in amounts of from 3 to 30% by weight relative to said zeolite.

8. The process of claim 1, wherein said halogenating is carried out at a temperature of from 0° C. to the boiling point of the reaction mixture.

9. The process of claim 1, wherein said halogenating is carried out at a temperature of from 20° C. to 100° C.

10. The process of claim 1, wherein R is a $C_{1-4}$ alkyl group or a chlorine atom.

11. The process of claim 1, wherein said benzene compound of formula (II) is toluene.

12. The process of claim 1, wherein said benzene compound of formula (II) is chlorobenzene.

13. The process of claim 1, wherein said zeolite is a L-type zeolite.

* * * * *